United States Patent
Lum et al.

(10) Patent No.: US 6,660,018 B2
(45) Date of Patent: Dec. 9, 2003

(54) MULTIPLE LANCET DEVICE

(75) Inventors: Paul Lum, Los Altos, CA (US); Michael Greenstein, Los Altos, CA (US); Leslie A. Leonard, Portoa Valley, CA (US); Dominique M Freeman, Pescadero, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 0 days.

(21) Appl. No.: 09/846,139

(22) Filed: Apr. 30, 2001

(65) Prior Publication Data

US 2001/0027328 A1 Oct. 4, 2001

Related U.S. Application Data (63) Continuation of application No. 09/264,341, filed on Mar. 8, 1999, now abandoned.

(51) Int. Cl.[7] ............................................. A61B 17/14
(52) U.S. Cl. ....................................... 606/181; 600/576
(58) Field of Search ........................... 606/44, 116, 131, 606/132, 167, 181, 182, 183, 185, 186, 187, 189; 604/19, 22, 27, 28, 46, 164.01, 187, 272–274, 540, 317, 403, 411; 600/573, 576–579

(56) References Cited

U.S. PATENT DOCUMENTS

| 5,611,810 A | * | 3/1997 | Arnold et al. ............... 606/185 |
| 5,643,308 A | * | 7/1997 | Markman ..................... 606/187 |
| 5,931,794 A | * | 8/1999 | Pitesky ......................... 600/556 |
| 6,083,196 A | * | 7/2000 | Trautman et al. ............. 606/46 |

* cited by examiner

Primary Examiner—Glenn K. Dawson (57) ABSTRACT

A device for puncturing the skin of a patient. The device includes first and second protrusions, each protrusion puncturing the skin when pressed against the skin. The first and second protrusions are arranged such that the first protrusion punctures the skin at a location less than a predetermined distance from the second protrusion. The distance is chosen to be less than the discriminatable distance between distinct pain perception points in the patient, such that the patient perceives a single puncture when the first and second protrusions puncture the skin. In one embodiment of the invention, the device includes a base lip that applies a lateral force to the skin when the base lip is pressed against the skin. In this embodiment, the protrusions are pressed into the skin as the base lip is pressed against the skin.

23 Claims, 6 Drawing Sheets

MULTIPLE LANCET DEVICE

This is a continuation of application Ser. No. 09/264,341, filed Mar. 8, 1999, now abandoned.

FIELD OF THE INVENTION

The present invention relates to devices for penetrating the skin to extract blood or other fluids, and more particularly, to a skin-pricking device having multiple penetrating tips.

BACKGROUND OF THE INVENTION

Medical tests that require a small volume of blood are well known. For example, home test kits for measuring blood sugar levels are utilized by diabetics. These test kits require that a drop of blood be placed on a test strip that is then inserted into a measurement apparatus that displays the glucose concentration in the blood sample. To obtain the drop of blood, the user is supplied with a lancet device, which makes a skin prick, typically in the user's finger. It would be advantageous to minimize the physical discomfort associated with this skin prick to obtain an amount of blood adequate for the test.

To successfully obtain blood, a piercing device must traverse the skin's various layers to reach the blood vasculature. Human skin is composed of a tough, keratinized squamous epithelium. The outermost layer of skin is known as the epidermis (0.07 to 0.12 mm thick), and has its own distinct layers: stratum corneum, stratum lucidum, stratum granulosum, stratum spinosum, and stratum basale. (For a review about skin, see Tortora and Anagnostakos *"Principles of anatomy and Physiology,"* Harper and Row 1981). Underneath the epidermis is the dermis, which is 1 to 2 mm thick. Because of its varying elasticity and the thickness due to the cellular structure and anatomical locations, the force necessary for penetrating the epidermis to access the vascular beds within the dermis layer will vary. It has been reported that skin tension is the greatest in the areas where the epidermal elastic keratinous fibers are dense, particularly in regions where the skin is thick, such as is found in the epigastric (stomach) regions.

The amount of force necessary to penetrate the skin surface will depend on the force applied normal to the surface of the skin needed to exceed the rupture strength. There exists an elastic range within which the degree of deflection corresponds directly with the applied force (skin depression). When the rupture limit is exceeded, a non-linear response by the skin (otherwise known as the inelastic response) occurs, corresponding to the further stretching of the skin at the point of application prior to rupture. The applied force reaches a maximum when the skin ruptures, resulting in the penetration of the object into the skin. The capillary bed under the dermis is approximately 300 to 750 microns below the outer surface of the skin in the areas of the fingers, the forearms and the abdomen. Bleeding occurs when the penetration of the object reaches the capillary bed.

Pain in blood sampling due to the skin being pierced is thought to be generated, in part, through pressure waves that are built up at the site of puncture. Many factors affect the pain sensation. Minimizing the incision angle of penetration, and hence the pressure wave buildup, would help reduce the pain sensation on sampling. In addition to the force required to penetrate the skin, the depth of penetration affects the sensation of pain as well. Optimizing these factors to reduce patient discomfort will encourage compliance to self test, for example, for diabetic self-monitoring.

A successful method to minimize pain generation due to skin puncture by a needle, pin or lancet, would be to minimize the area over which the puncture occurs. This can be achieved by miniaturizing the needle or lancet, provided the force applied to create the wound is small. The smaller the needle, the less force is required to puncture the skin, and fewer nerve endings are stimulated by the cut. Unfortunately, there is a lower limit on the size of the needle, since smaller needle pricks produce less blood than larger needle pricks, and there is a minimum amount of blood that must be extracted for any given test or analytical procedure.

Certain lancets have been used for special purposes. For example, needle devices with multiple needles have been used in a Hear Test (tuberculin test), as was described in U.S. Pat. No. 5,611,809 (Marshall et al.), to carry a substance smeared on the skin surface into the blood vessels. However, this device is aimed specifically at injecting a sufficient amount of immunogen into the skin. The multiple needles provide a larger surface area to deliver a larger dose of the substance into the puncture wounds than a single larger needle. This design was seen to be generally applicable to vaccination, and is very similar to U.S. Pat. No. 4,109,655 (Chacornac), which describes a multi-penetration vaccination apparatus. The Chacornac vaccination apparatus has concentric sleeves with points for skin penetration. The points are dipped into a vaccine, which is then delivered into the skin by the points.

In the prior vaccination technology, when multiple needle pricks are used on a patient, the patient perceives the multiple needle pricks. For vaccination, despite the discomfort, being pricked a number of times and at a number of different locations is acceptable. These techniques are intended for carrying vaccines into tissue, not for withdrawing or extracting fluid from the pricked tissue.

For fluid (e.g. blood) sampling, there is still a need for a technique that can extract an adequate amount of blood with minimal discomfort to the patient.

SUMMARY OF THE INVENTION

The present invention provides a technique for extracting blood from the skin of a user with reduced discomfort. In one aspect, a device for puncturing the skin of a patient is provided. The device includes two or more protrusions. Each protrusion punctures the skin when it is pressed against the skin. At least two, preferably all, of the protrusions are arranged such that a first protrusion punctures the skin at a location equal or less than a predetermined distance from a neighboring protrusion. The distance is chosen such that the patient perceives a single puncture when the first and the neighboring protrusions, and preferably all of the protrusions, puncture the skin. In one embodiment of the invention, the device includes a base assembly that applies a lateral force to the skin when the base assembly is applied against the skin, thereby causing the skin to be taut. In this embodiment, the protrusions are pressed into the skin as the base assembly is pressed against the skin.

The present invention provides a technique by which a user perceives a single puncture when sampling blood when in fact two or more punctures are administered. This technique thus reduces the discomfort to the user while ensuring adequate sampling of fluid (e.g., blood) from the puncture wounds. To this end, the present invention provides an improved lancet device having multiple lancets with at least two, preferably all, of the lancets being less than or equal to the critical distance apart from one another.

Further, the present invention provides better control on the depth of penetration of the lancet by increasing the tautness of the skin for the puncture to occur. This increase of tautness can be implemented by pushing the skin with a lateral force component at locations surrounding a central site where lancet penetration occurs. The increase in tautness reduces the uncertainty of the depth of penetration by the lancet into the skin as a result of the amount of imperfections in the skin, such as wrinkles. Further, in another embodiment, varying the length of the protrusions, for example, having longer protrusion on the inside, accomplishes a more uniform penetration and therefore better fluid sampling by the protrusions.

DETAILED DESCRIPTION OF THE INVENTION

The present invention involves a technique to reduce discomfort to a patient during lancing of the patient's skin. The technique is based upon the ability of the human body to distinguish the distance between multiple, simultaneous punctures. For any given location on a patient's body, there is a different critical distance for distinguishing between two individual puncture points. A puncture by two lancets that are closer than this critical distance is perceived by the patient as a single puncture. The critical distance is smallest on the fingers, being approximately 2 to 3 mm at the tips of the fingers. (See, Lawrence Krueger, *Pain and Touch*, FIG. 1, Academic Press, San Diego, 1996). As used herein, the term "lancet" refers to an elongated object with a sharp point for inserting into the skin to induce bleeding. Such a lancet may be needle-like with a round cross-section, or it may have cutting edge(s) along its elongated body for a cutting action to split the tissue. When the term "lance," "puncture," "prick" or "penetrate" is used herein regarding a lancet, unless specified otherwise, it is to be understood that any of such lancets may be used.

It has been found experimentally that a person cannot perceive multiple needles that are placed closer together than about 3 mm when the needles are used to puncture the skin on the patient's finger tip. (See FIG. 1A for data obtained on the ability of human subjects to distinguish between one and two needles in puncturing the skin. In the figure, the abscissa shows the individuals being evaluated and the ordinate shows the critical distance in mm below which the individual cannot discriminate between two pricking points.) Accordingly, a puncture by a multiple needle lancet device having needles that are less than 2 to 3 mm apart is perceived to be a puncture by a single needle by the user. In the area of the finger tips, preferably, the distance between any two lancets is less than about 1.65 mm. This arrangement provides an adequate space between lancets of, for example, 30 to 34 gauge (290 microns to 220 microns) needles. Since skin in other areas of the body is generally less sensitive than finger tips, often lancets can be arranged to be separated by more than 3 mm between two individual lancets and still produce the sensation of only one puncture when the lancet device is applied to puncture the skin. By limiting the distance between lancets to equal or less than the critical distance of the particular area of the skin, the present invention provides lancet devices which result in less pain.

Figure 1A:
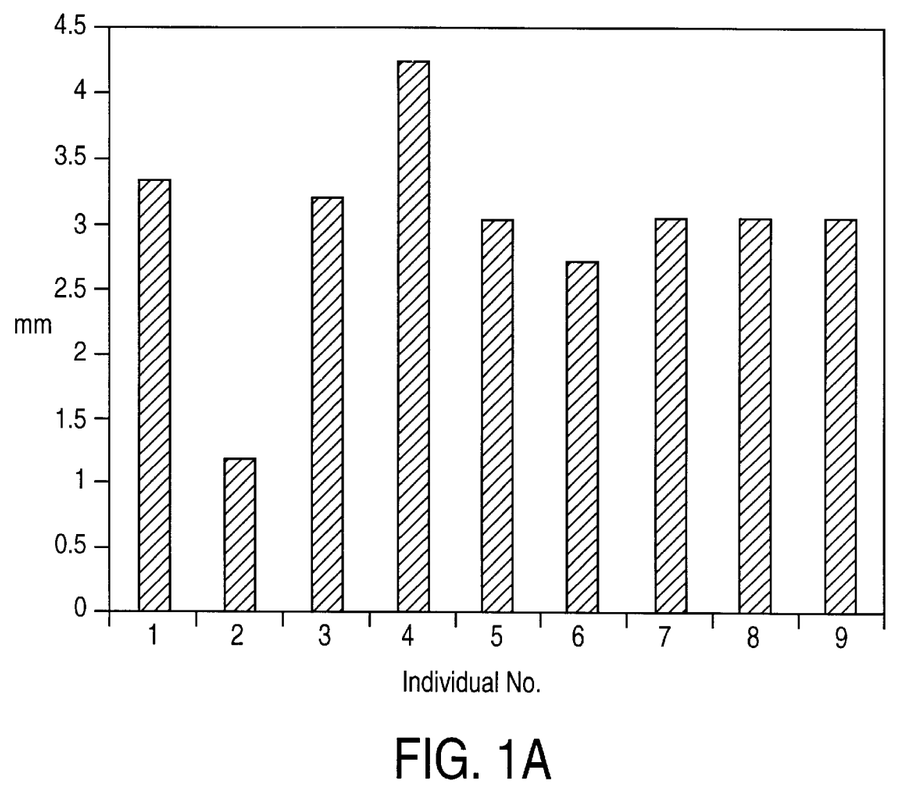
FIG. 1A is a graphical depiction of the ability of individuals to discriminate pricking points on the skin.
Figure 1B:
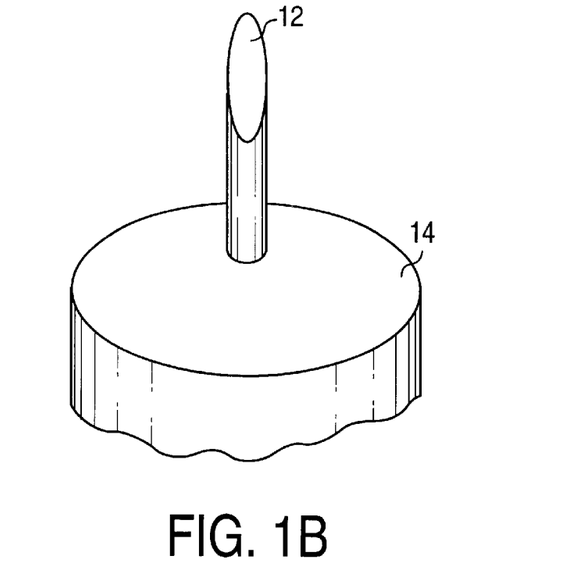
FIG. 1B is an isometric view of a needle of a multiple needle lancet device according to the present invention.
Figure 1C:
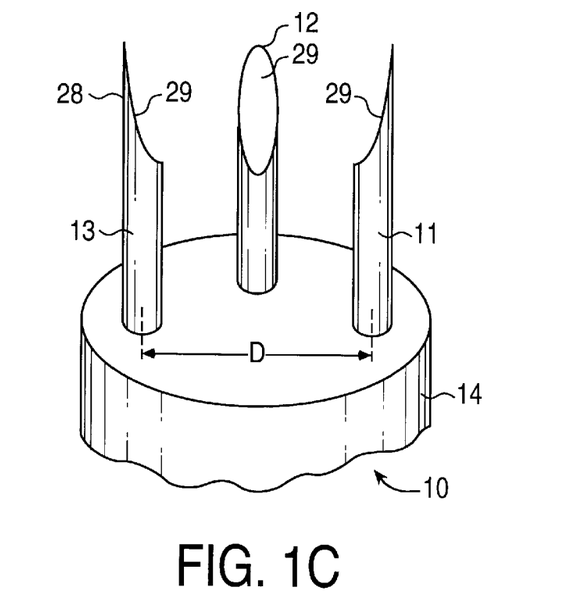
FIG. 1C is an isometric view of an embodiment of a multiple needle lancet device according to the present invention.

FIG. 1B shows an isometric view of an isolated needle 12 supported by a support body 14 in a lancet device of the present invention. FIG. 1C is a perspective view of a to multiple needle lancet device 10 according to the present invention. The lancet device 10 has three needles 11, 12, 13 whose tips are within a circle. The distance, D, between any two of the needles 11–13 is chosen such that D is less than critical distance for the site on the patient's body at which the puncture is to be performed. In a preferred embodiment of the present invention, three needles are spaced about 1.6 mm from each other and are supported by body 14. Thus, they are arranged in a triangular configuration. For a three-needle lancet device, needles of 220 microns (34 gauge) in diameter would ensure that the distance, D, is less than or equal to the critical distance and the lancet device can be used to obtain adequate blood sampling.

Although in the above embodiment three needles are used, other numbers of needles and placement arrangements may be utilized provided the needles are arranged such that all of the puncture wounds occur within the area (for example, a circular area) such that the distance between any two needles is less than the critical distance. For example, an alternative embodiment includes 4 or more needles arranges in a ring, i.e., as the vertices of a polygon. The needles can be located on the circumference of a circle which constitutes the ring. It is preferred that the circle has a diameter equal or smaller than the critical distance for pain discrimination so that a puncture by the device will be perceived as a puncture by a single lancet. However, it is contemplated that alternatively the distance from a first needle to some of the other needles can be larger than the critical distance, as long as the distance between the first needle and one other needle is less than the critical distance, thereby rendering these two needles indiscriminatable during the lancing of the skin. Generally, the total lancing foot print of the lancets of the lancet device on the skin would be less than about 4 mm, preferably less than 3 mm, more preferably less than 2 mm, from one side of a lancet to the to the remote side of another lancet remote therefrom. In this way, when punctured by such a lancet device, the user may perceive the two needles as only one needle. This will result in less pain being felt by the patient.

Figure 1D:
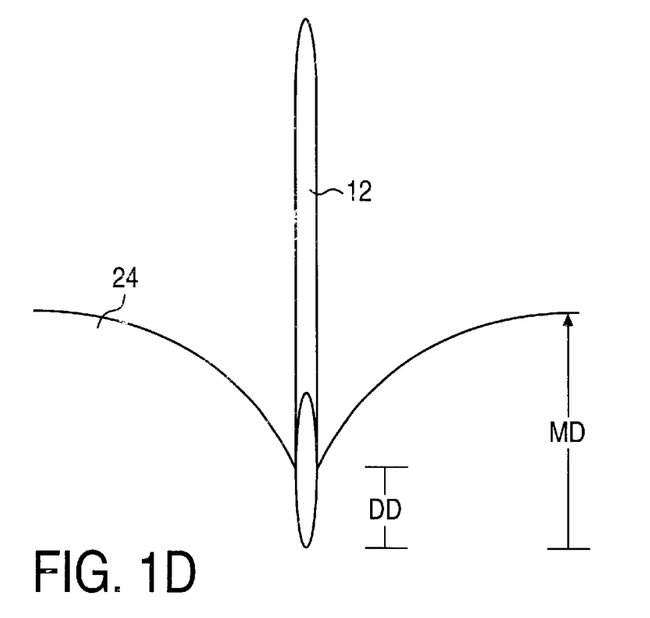
FIG. 1D and FIG. 1E are schematic views showing how a needle punctures the skin.
Figure 1E:
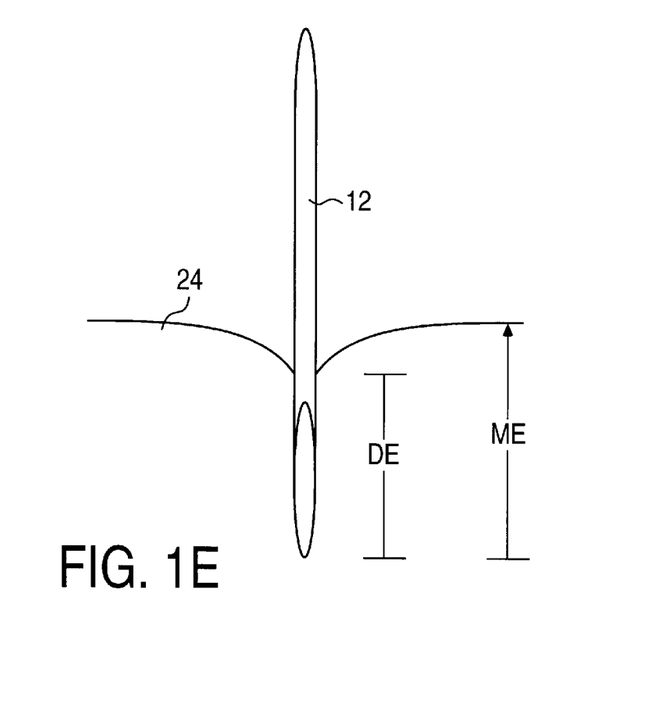

For any given lancet, the condition of the skin has a significant effect on the penetration of the lancet into it. For example, if the skin is wrinkled, from the time the lancet touches the skin to the time it punctures it, the lancet may have traveled a considerable distance. This is because the lancet stretches the wrinkled skin until the skin is taut enough and the lancet pressure on the skin exceeds a threshold (the "puncture threshold") to penetrate. This is shown in FIG. 1D. After the lancet has begun to penetrate the skin 24, due to the lack of tautness, the depth of lancet penetration into the skin cannot be easily controlled. The arrows DD shows the depth of penetration of the lancet for the amount of lancet forward movement of arrows MD. In contrast, for skin that is taut, as shown in FIG. 1E, the needle 12 penetrates the skin 24 a distance shown by arrows DE for a needle with a forward movement of a distance of ME. Therefore, it is easier to control the depth of lancet penetration when the skin is held taut prior to moving the lancet forward against the skin 24.

Figure 2:
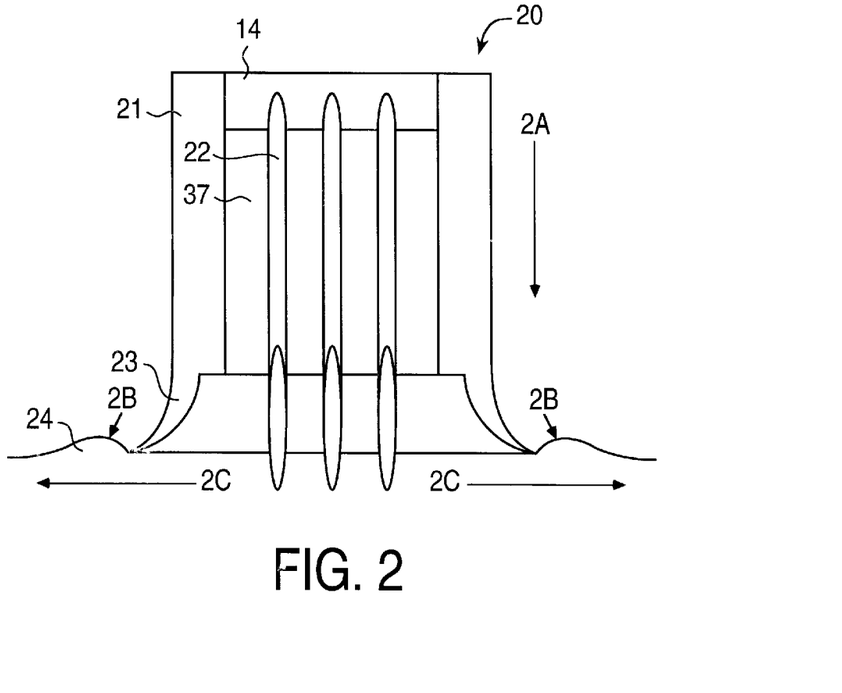
FIG. 2 is a sectional view of one embodiment of a lancet assembly according to the present invention with a lip for rendering the skin taut.

The depth of the puncture will be less than expected if the skin is not held taut during the puncture. Accordingly, a preferred embodiment of the present invention includes a structure that stretches the skin for the puncture. FIG. 2 shows a sectional view of a lancet assembly 20 according to the present invention. Lancet assembly 20 includes a central cylinder 21, which carries the needles 22. Assembly 20 has a flexible, resilient base lip 23 which is constructed from a material having a high coefficient of friction with respect to the patient's skin 24. Connected to and supported by the central cylinder 21, the base lip 23 is approximately ring-shaped and flares slightly outwards, i.e., away from the center of the ring (i.e., the axis of the assembly 20). When assembly 20 is held to touch the skin 24, it rests against the skin such that the base lip 23 assumes a ring shape contact at a rest-state diameter, which may be about D in an embodiment of FIG. 1. When the assembly 20 is pressed against the skin, the base lip 23 of assembly 20 flexes and pushes the skin laterally (outwardly away from the center of the base lip 23) such that the skin is rendered taut and the needles are lowered into the skin as the assembly 20 is moved downward, as shown in FIG. 2. Arrow 2A represents the downward pressure applied to the assembly 20. Arrows 2B shows the resultant oblique force by the base lip 23 on the skin 24. Arrows 2C show the lateral resultant force on the skin 24 to increases the tautness of the skin. The resilient nature of the base lip 23 prevents the base lip 23 from collapsing as the assembly 20 is pressed against the skin. In an alternative embodiment, the top of the body 14 can move (e.g., slide) relative to the central cylinder 21 such that the assembly 20 can be held against the skin and the top of the body 14 pressed to drive the lancets into the skin.

The material of construction of the base lip can be any resilient, flexible material with adequate coefficient of friction with the skin. Suitable materials include polymeric substances such as latex rubber, butyl rubber, silicone, and the like.

Figure 3:
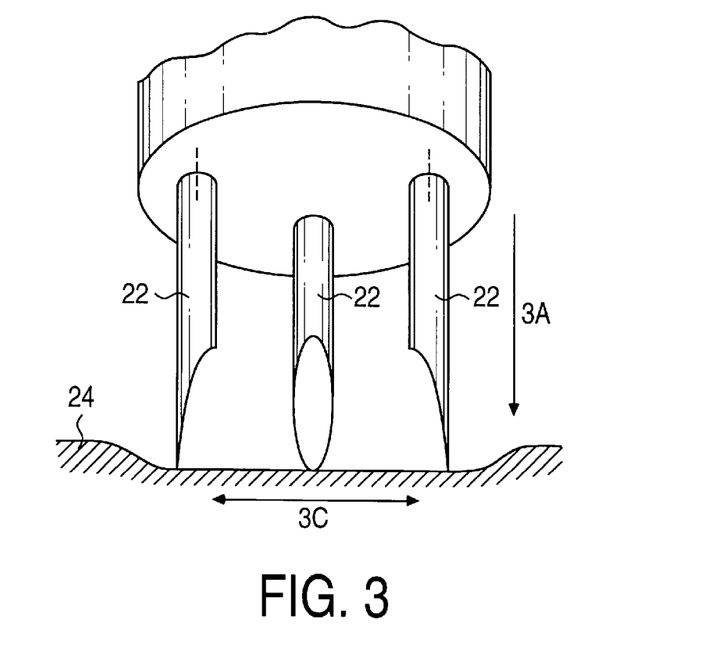
FIG. 3 is a sectional view of the lancet assembly shown in FIG. 2 after the assembly has been pressed against the skin.

FIG. 3 shows how the tautness of the skin can be increased by a group of lancets arranged on the circumference of a circle as the lancets are pressed on the skin 24. Arrow 3A shows the downward pressure on the lancets 22. Arrows 3C show the lateral directing force increasing the tautness as a result of the lancets 22 pushing on the skin 24.

Figure 4:
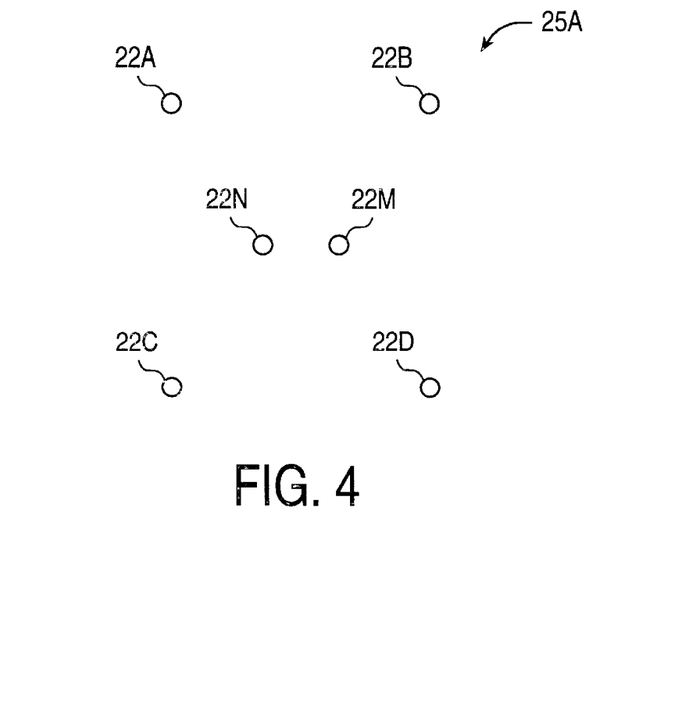
FIG. 4 is schematic representation of the grouping of lancets in a lancet device with one group surrounding another group of lancets.

The above-described embodiments of the present invention utilize needles having the same length. However, in other embodiments (see, for example, FIG. 4), the needles may be grouped in groups having different lengths to improve the uniformity of penetration. In certain embodiments of the invention, the needles are placed in concentric groupings with the longer needles on the inside of the groupings. FIG. 4 shows a schematic bottom view of an assembly 25A having four needles 22A, 22B, 22C, 22D in a group encircling two central needles 22M, 22N. Such an arrangement reduces the problems associated with maintaining the skin taut in the center of the area during the puncture. The inner needles are able to penetrate sufficiently given the concave nature of the skin if not ideally taut.

Figure 5:
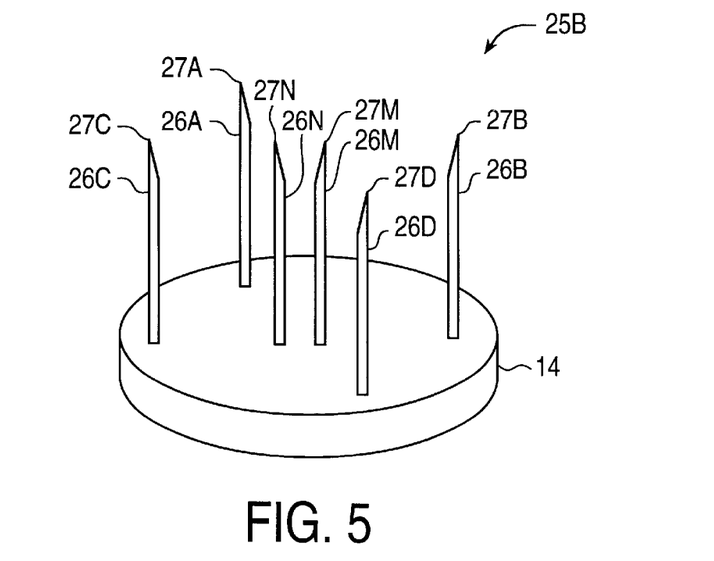
FIG. 5 shows an isometric view of an embodiment of the present invention with longer central lancets.

In the embodiment shown in FIG. 5, an assembly 25B can include central lancets 26M, 26N, that are longer than the lancets 26A, 26B, 26C, 26D in the group surrounding them. An assembly of this kind offers the advantage that all the lancets can puncture to a similar depth into the skin. If the lancets are same length, when pressed against the skin, due to wrinkles, or the elasticity of the skin that allows the skin farther away from the base lip to move, the circumferential lancets (i.e., lancets 26A, 26B, 26C, 26D) would tend to puncture the skin before the central lancets 26M, 26N. Further, as shown in FIG. 5, the lancets can have off center sharp tips 27A, 27B, 27C, 27D, 27M, 27N arranged such that the sharp tips are facing away from the center of the group. In this way, as the lancets penetrate into the skin, they assist to maintain the tautness of the skin. In one embodiment, the off-center sharp tip is the result of a beveled end such as those shown in FIG. 1C. The longer sides 28 of the lancets face the outside of the device and the bevels 29 in FIG. 1C face inwardly toward the center of the group of lancets.

Figure 6:
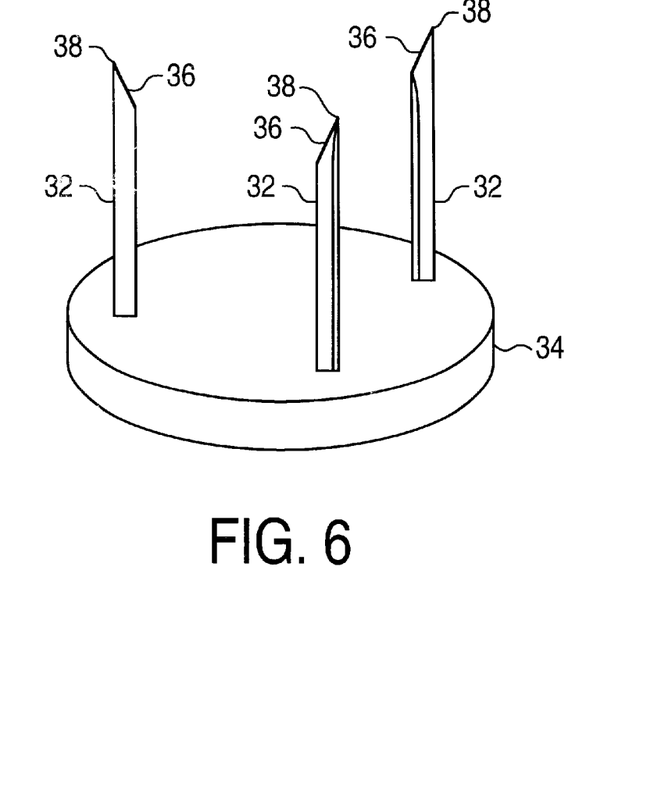
FIG. 6 shows an isometric view of an embodiment of a lancet device with lancets having cutting a edge and sharp tips.

In an alternative shown in FIG. 6, the lancets 32 in the lancet device 34 each have a oblique cutting edge 36 leading to a sharp point 38. The oblique cutting edges 36 each face inwardly, i.e., toward the axis of the device during the lancing process. The sharp point 38 and the cutting edge 36 facilitate the efficient penetration of the lancet into the skin without tearing, thus reducing the amount or intensity of pressure waves propagating outward from the point of penetration and the pain, as well as provides for better healing condition after the lancet has been withdrawn.

The lancets used in the lancet device may be needles, which can be hollow or solid without departing from the teachings of the present invention. Hollow needles may be preferred in those applications in which the blood sample is to be extracted by the lancet device for direct transfer to the blood testing system. Hollow needles can be used to conduct the blood sample either by capillary action, by the pressure within the skin, or by connecting the needles to a suction device. If when the lancet device is pressed onto the skin a collection chamber is present (e.g., central cylinder 21, top 14, base lip 23 and the skin form a collection chamber 37 shown in FIG. 2.), blood, or other fluid from the skin, can be collected and transported to a desired location, for example, by further capillary action or by suction.

Figure 7:
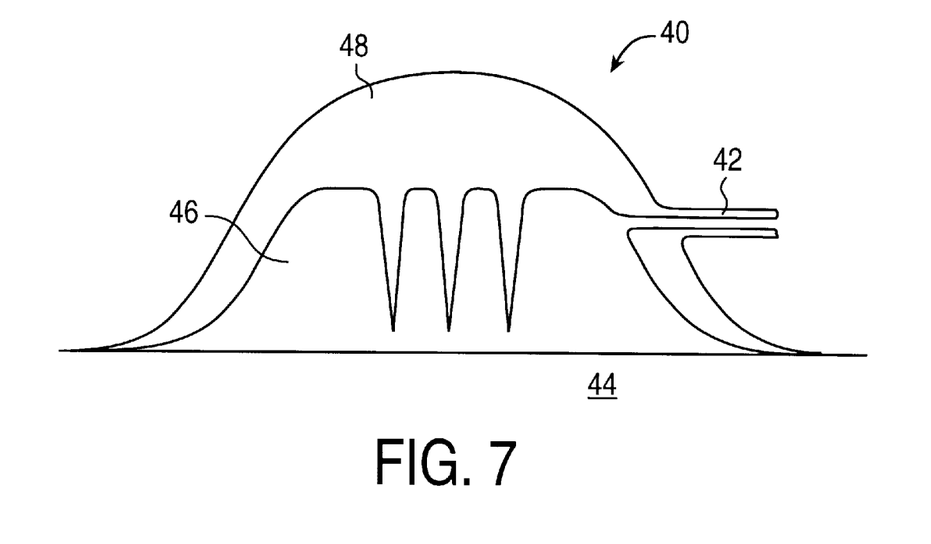
FIG. 7 shows a sectional view of an embodiment of a lancet device with body having an outlet to conduct blood away.

FIG. 7 depicts an embodiment of a lancet device 40 having an outlet 42, which can be connected to a capillary or a suction. When pushed against the skin 44, the lancet device 40 forms a chamber 46 between the body 48 and the skin 44. The chamber has an outlet 42 for conducting blood out of the chamber 46. Blood leaving the outlet 42 can be conducted to an analyzer for analysis of the physical and chemical characteristics of the blood, such as optical properties, hemoglobin content, gas content, ionic content, glucose content, pH, etc. Suction devices and capillary devices that can be used for such applications are described in copending patent application Ser. No. 09/264,597, entitled "Extraction and transportation of blood for analysis," invented by Lum et al., filed on even date with and assigned to the same assignee as the present application), which is incorporated by reference in its entirety herein.

Although the above-described embodiments of the present invention have been described in terms of lancets using "needles" as a preferred embodiment, other forms of puncture devices may be utilized. For example, the puncture devices could be in the form of small oblong blades. Various modifications to the present invention will become apparent to those skilled in the art from the foregoing description and accompanying drawings.

What is claimed is:

1. A device for puncturing the skin of a patient to sample body fluid, said device comprising two or more protrusions including a first protrusion and a second protrusion, each protrusion having a diameter of at least about 200 microns and a separate distal point and puncturing the skin to result in separate puncture wounds when pressed against the skin, at least the first protrusion being arranged such that it punctures the skin at a location at a distance at most 4 mm away from the second protrusion nearest thereto, wherein said device comprises a base assembly associated with said protrusions, said base assembly applying a force having a lateral component to said skin when said base assembly is pressed agains said skin, wherein the protrusions are movable relative to the base assebly.

2. A device according to claim 1 wherein said protrusions are forced into said skin when said base assembly is pressed against said skin.

3. A device according to claim 1 wherein said base assembly comprises a resilient material that is deformed when said base assembly is pressed against said skin.

4. A device according to claim 1 wherein the base assembly includes a border lip surrounding the protrusions such that when pressed against the skin the border lip exerts force on the skin with a component of the force away from the protrusions.

5. A device according to claim 1 wherein said first and second protrusions each comprise a hollow member.

6. A device according to claim 1 wherein each protrusion has a sharp tip off center on the protrusion and a side of each protrusion having the sharp tip on each of the protrusions being arranged to face away from the axis of the lancet device.

7. A device according to claim 6 wherein each protrusion has a beveled end leading to said sharp tip, the bevel of each protrusion facing inwards from the axis of the lancet device.

8. A device according to claim 1 wherein there are three or more protrusions that are hollow to permit fluid flow therein.

9. A device according to claim 1 wherein each protrusion is at most 3 mm away from another of the protrusions in said device.

10. A device for puncturing the skin of a patient to sample body fluid, said device comprising two or more protrusions including a first protrusion and a second protrusion, each protrusion having a diameter of at least about 200 microns and a separte distal point and puncturing the skin to result in separate puncture wounds when pressed against the skin, at least the first protrusion being arranged from the second protrusion nearest thereto, wherein three or more protrusions are hollow to permit fluid flow therein, and wherein said device comprises a chamber in fluid communication with the hollow protrusions, the chamber having an exit having fluid communication to outside the device for access to a suction or capillary force.

11. A device according to claim 10 wherein some of the protrusions are distributed at polygonal vertices equidistance from the axis and surrounding one or more protrusions nearer to the axis, the polygonal vertices protrusion having a different length from the one or more protrusions nearer to the axis of the lancet device.

12. A device according to claim 11 wherein the protrusions at polygonal vertices surround and are shorter than at least two protrusions that are near the axis of the lancet device.

13. A device according to claim 10 comprising more than three protrusions, and the protrusions are not of equal length.

14. A method of making a lancet device for puncturing the skin of a patient to sample body fluid, comprising:

arranging on a support body two or more protrusions each having a diameter of at least about 200 microns and a separate distal point such that at least one protrusion punctures the skin at a location at a distance D at most 4 mm from another of the protrusions nearest to said one protrusion to result in separate puncture wounds when the protrusions are pressed against the skin;

forming on each protrusion a sharp tip off center on the protrusion; and arranging the sharp tips of the protrusions to face away from the axis of the lancet device.

15. A method according to claim 14 further comprising attaching a base assembly to said protrusions such that said base assembly has a flare member angled away from the axis of the support body, the flare member applying a force with a lateral component to said skin when said base assembly is pressed against said skin.

16. A method according to claim 14 wherein said protrusions are connected to the base assembly such that the protrusions are forced into said skin when said base assembly is pressed against said skin and wherein said base assembly comprises a resilient material that is deformed when said base assembly is pressed against said skin.

17. A method according to claim 14 comprising forming said base assembly with a resilient material such that the base assembly is deformable when said base assembly is pressed against said skin.

18. A method according to claim 14 further comprising providing on the base assembly a border lip surrounding the protrusions such that when pressed against the skin the border lip exerts force on the skin with a component of the force away from the protrusions.

19. A method according to claim 14 further comprising locating some of the protrusions at polygonal vertices equidistance from the axis and surrounding one or more of the other protrusions nearer to the axis of the lancet device, the polygonal vertex protrusions having a different length from the one or more protrusions nearer to the axis of the lancet device.

20. A method according to claim 14 wherein each protrusion is at most 3 mm away from another of the protrusions.

21. A method of using a lancet device to puncture the skin of a patient to sample body fluid, comprising:

driving two or more protrusions having a diameter of at least about 200 microns, to puncture the skin such that at least one protrusion punctures the skin at a location a distance D from another of the protrusions nearest thereto when the protrusions are pressed against the skin, said distance D being chosen to be at most 4 mm so as to be less than the discriminatable distance between the distinct pain preception points in the patient, wherein each protrusion has a sharp tip off center on the protrusion such that the side of the protrusion having the sharp tip in each protrusion faces away from the axis of the lancet device when the lancet is being driven into the skin.

22. A method according to claim 21 further comprising pressing a base assembly to push said protrusions to penetrate the skin and to apply a force with a lateral component to said skin to increase tautness of the skin.

23. A method according to claim 21 wherein each protrusion is at most 3 mm away from another of the protrusions.

* * * * *